United States Patent [19]

Bouchard et al.

[11] Patent Number: 5,773,291
[45] Date of Patent: Jun. 30, 1998

[54] NON-MELANOTYTIC MAMMALIAN CELL CONSTITUTIVELY EXPRESSING BIOLOGICALLY ACTIVE HUMAN TYROSINASE AND USE THEREOF

[75] Inventors: Brigitte Bouchard; Alan N. Houghton, both of New York, N.Y.

[73] Assignee: Sloan-Kettering Institute for Cancer Research, New York, N.Y.

[21] Appl. No.: 376,306

[22] Filed: Jan. 23, 1995

Related U.S. Application Data

[63] Continuation of Ser. No. 166,601, Dec. 13, 1993, abandoned, which is a continuation of Ser. No. 8,255, Jan. 25, 1993, abandoned, which is a continuation of Ser. No. 594,310, Oct. 9, 1990, abandoned, which is a continuation-in-part of Ser. No. 343,960, Apr. 26, 1989, abandoned.

[51] Int. Cl.$^6$ .............................. C12N 5/10; C12N 5/16; C12N 5/18; C12N 5/22
[52] U.S. Cl. ......................... 435/325; 435/352; 435/357; 435/363; 435/366; 435/128; 435/133; 435/189
[58] Field of Search .............................. 435/69.1, 69.51, 435/121, 128, 133, 136, 172.1, 172.3, 189, 190, 191, 240.1, 240.2, 240.23, 320.1, 948, 325, 352, 357, 363, 36, 366; 935/14, 18, 23, 28, 32, 66, 69, 70

[56] References Cited

U.S. PATENT DOCUMENTS 4,745,051   5/1988   Smith et al. ..................... 435/69.51
5,529,909   6/1996   della-Cioppa et al. ................ 435/69.7

FOREIGN PATENT DOCUMENTS 0213898   11/1987   European Pat. Off. .

OTHER PUBLICATIONS

Bouchard, B. et al. Journal of Experimental Medicine 169: 2029–2042 (Exhibit B).
Muller, G. et al. EMBO 7 (9): 2723–2730 (Exhibit C).
Shibahara, S. et al. Nucleic Acid Research 14 (6): 2413–2417 (Exhibit D).
Takeda, A. et al. Biochemical and Biophysical Research Communications 162 (3): 984–990 (Exhibit E); and.
Wigler, M. et al. Cell 16: 777–785 a(Exhibit F).
Kwon et al, Isolation and sequence of cDNA Clone for human tyrosinase that maps at the mouse calbino locus, PNAS, v. 84, 7473–77, 1987.
Winnacker, From Genes to Clones, Introduction to Gene Technology, "Gene expression in Eukanyotes" pp. 193–204, 1988.

*Primary Examiner*—Keith D. Hendricks
*Attorney, Agent, or Firm*—John P. White

[57] ABSTRACT

This invention provides a non-melanocytic eucaryotic cell constitutively expressing biologically active human tyrosinase. The present invention also provides methods of producing biologically active human tyrosinase. Additionally, the invention provides a non-melanocytic eucaryotic cell which constitutively expresses biologically active human tyrosinase which in turn catalyzes the production of melanin. The melanin so produced may then be recovered.

7 Claims, 13 Drawing Sheets

FIG. 1A

```
-19  Gly Arg Met Leu Leu Ala Val Leu Tyr
  1  GGA AGA ATG CTC CTG GCT GTT TTG TAC
         ---                              -1 ↓ +1
     Cys Leu Leu Trp Ser Phe Gln Thr Ser Ala Gly
     TGC CTG CTG TGG AGT TTC CAG ACC TCC GCT GGC

2  His Phe Pro Arg Ala Cys Val Ser Ser
 61  CAT TTC CCT AGA GCC TGT GTC TCC TCT

Lys Asn Leu Met Glu Lys Glu Cys Cys Pro Pro
     AAG AAC CTG ATG GAG AAG GAA TGC TGT CCA CCG

22  Trp Ser Gly Asp Arg Ser Pro Cys Gly
121  TGG AGC GGG GAC AGG AGT CCC TGT GGC

Gln Leu Ser Gly Arg Gly Ser Cys Gln Asn Ile
     CAG CTT TCA GGC AGA GGT TCC TGT CAG AAT ATC

42  Leu Leu Ser Asn Ala Pro Leu Gly Pro
181  CTT CTG TCC AAT GCA CCA CTT GGG CCT

Gln Phe Pro Phe Thr Gly Val Asp Asp Arg Glu
     CAA TTT CCC TTC ACA GGG GTG GAT GAC CGG GAG

62  Ser Trp Pro Ser Val Phe Tyr Asn Arg
241  TCG TGG CCT TCC GTC TTT TAT AAT AGG
                                     --------
     Thr Cys Gln Cys Ser Gly Asn Phe Met Gly Phe
     ACC TGC CAG TGC TCT GGC AAC TTC ATG GGA TTC
     ---
 82  Asn Cys Gly Asn Cys Lys Phe Gly Phe
301  AAC TGT GGA AAC TGC AAG TTT GGC TTT

Trp Gly Pro Asn Cys Thr Glu Arg Arg Leu Leu
     TGG GGA CCA AAC TGC ACA GAG AGA CGA CTC TTG
                         ------------
102  Val Arg Arg Asn Ile Phe Asp Leu Ser
361  GTG AGA AGA AAC ATC TTC GAT TTG AGT

Ala Pro Glu Lys Asp Lys Phe Phe Ala Tyr Leu
     GCC CCA GAG AAG GAC AAA TTT TTT GCC TAC CTC

122  Thr Leu Ala Lys His Thr Ile Ser Ser
421  ACT TTA GCA AAG CAT ACC ATC AGC TCA

Asp Tyr Val Ile Pro Ile Gly Thr Tyr Gly Gln
     GAC TAT GTC ATC CCC ATA GGG ACC TAT GGC CAA
```

FIG. 1B

```
142  Met Lys Asn Gly Ser Thr Pro Met Phe
481  ATG AAA AAT GGA TCA ACA CCC ATG TTT
                 -----------

Asn Asp Ile Asn Ile Tyr Asp Leu Phe Val Trp
     AAC GAC ATC AAT ATT TAT GAC CTC TTT GTC TGG

162  Ile His Tyr Tyr Val Ser Met Asp Ala
541  ATC CAT TAT TAT GTG TCA ATG GAT GCA

Leu Leu Gly Gly Tyr Glu Ile Trp Arg Asp Ile
     CTG CTT GGG GGA TAT GAA ATC TGG AGA GAC ATT

182  Asp Phe Ala His Glu Ala Pro Ala Phe
601  GAT TTT GCC CAT GAA GCA CCA GCT TTT

Leu Pro Trp His Arg Leu Phe Leu Leu Arg Trp
     CTG CCT TGG CAT AGA CTC TTC TTG TTG CGG TGG

202  Glu Gln Glu Ile Gln Lys Leu Thr Gly
661  GAA CAA GAA ATC CAG AAG CTG ACA GGA

Asp Glu Asn Phe Thr Ile Pro Tyr Trp Asp Trp
     GAT GAA AAC TTC ACT ATT CCA TAT TGG GAC TGG
                 -----------
222  Arg Asp Ala Glu Lys Cys Asp Ile Cys
721  CGG GAT GCA GAA AAG TGT GAC ATT TGC

Thr Asp Glu Tyr Met Gly Gly Gln His Pro Thr
     ACA GAT GAG TAC ATG GGA GGT CAG CAC CCC ACA

242  Asn Pro Asn Leu Leu Ser Pro Ala Ser
781  AAT CCT AAC TTA CTC AGC CCA GCA TCA

Phe Phe Ser Ser Trp Gln Ile Val Cys Ser Arg
     TTC TTC TCC TCT TGG CAG ATT GTC TGT AGC CGA

262  Leu Glu Glu Tyr Asn Ser His Gln Ser
841  TTG GAG GAG TAC AAC AGC CAT CAG TCT

Leu Cys Asn Gly Thr Pro Glu Gly Pro Leu Arg
     TTA TGC AAT GGA ACG CCC GAG GGA CCT TTA CGG
                 -----------
282  Arg Asn Pro Gly Asn His Asp Lys Ser
901  CGT AAT CCT GGA AAC CAT GAC AAA TCC

Arg Thr Pro Arg Leu Pro Ser Ser Ala Asp Val
     AGA ACC CCA AGG CTC CCC TCT TCA GCT GAT GTA
```

FIG. 1C

```
302  Glu Phe Cys Leu Ser Leu Thr Gln Tyr
961  GAA TTT TGC CTG AGT TTG ACC CAA TAT

Glu Ser Gly Ser Met Asp Lys Ala Ala Asn Phe
     GAA TCT GGT TCC ATG GAT AAA GCT GCC AAT TTC
                                         -------
322  Ser Phe Arg Asn Thr Leu Glu Gly Phe Ala Ser
1021 AGC TTT AGA AAT ACA CTG GAA GGA TTT GCT AGT
     ---
     Pro Leu Thr Gly Ile Ala Asp Ala Ser
     CCA CTT ACT GGG ATA GCG GAT GCC TCT

342  Gln Ser Ser Met His Asn Ala Leu His Ile Tyr
1081 CAA AGC AGC ATG CAC AAT GCC TTG CAC ATC TAT

Met Asn Gly Thr Met Ser Gln Val Gln
     ATG AAT GGA ACA ATG TCC CAG GTA CAG
     ------------
362  Gly Ser Ala Asn Asp Pro Ile Phe Leu Leu His
1141 GGA TCT GCC AAC GAT CCT ATC TTC CTT CTT CAC

His Ala Phe Val Asp Ser Ile Phe Glu
     Cat GCA TTT GTT GAC AGT ATT TTT GAG

382  Gln Trp Leu Arg Arg His Arg Pro Leu Gln Glu
1201 CAG TGG CTC CGA AGG CAC CGT CCT CTT CAA GAA

Val Tyr Pro Glu Ala Asn Ala Pro Ile
     GTT TAT CCA GAA GCC AAT GCA CCC ATT

402  Gly His Asn Arg Glu Ser Tyr Met Val Pro Phe
1261 GGA CAT AAC CGG GAA TCC TAC ATG GTT CCT TTT

Ile Pro Leu Tyr Arg Asn Gly Asp Phe
     ATA CCA CTG TAC AGA AAT GGT GAT TTC

422  Phe Ile Ser Ser Lys Asp Leu Gly Tyr Asp Tyr
1321 TTT ATT TCA TCC AAA GAT CTG GGC TAT GAC TAT

Ser Tyr Leu Gln Asp Ser Asp Pro Asp
     AGC TAT CTA CAA GAT TCA GAC CCA GAC

442  Ser Phe Gln Asp Tyr Ile Lys Ser Tyr Leu Glu
1381 TCT TTT CAA GAC TAC ATT AAG TCC TAT TTG GAA

Gln Ala Ser Arg Ile Trp Ser Trp Leu
     CAA GCG AGT CGG ATC TGG TCA TGG CTC
```

FIG. 1D

```
 462 Leu Gly Ala Ala Met Val Gly Ala Val Leu Thr
1441 CTT GGG GCG GCG ATG GTA GGG GCC GTC CTC ACT

Ala Leu Leu Ala Gly Leu Val Ser Leu
     GCC CTG CTG GCA GGG CTT GTG AGC TTG

482 Leu Cys Arg His Lys Arg Lys Gln Leu Pro Glu
1501 CTG TGT CGT CAC AAG AGA AAG CAG CTT CCT GAA

Glu Lys Gln Pro Leu Leu Met Glu Lys
     GAA AAG CAG CCA CTC CTC ATG GAG AAA

502 Glu Asp Tyr His Ser Leu Tyr Gln Ser His Leu
1561 GAG GAT TAC CAC AGC TTG TAT CAG AGC CAT TTA
     TAAAAGGCTTAGGCAATAGAGTAGGGCCAAAAAGC

1628 CTGACCTCACTCTAACTCAAAGTAATGTCCAGGTTCCCAGAGAATATCTGCTGG
     TATTTTTCTGTAAAGACCATTTGCA

1707 AAATTGTAACCTAATACAAAGTGTAGCCTTCTTCCAACTCAGGTAGAACACACC
     TGTCTTTGTCTTGCTGTTTTCACTC

1786 AGCCCTTTTAACATTTTCCCCTAAGCCCATATGTCTAAGGAAAGGATGCTATTT
     GGTAATGAGGAACTGTTATTTGTAT

1865 GTGAATTAAAGTGCTCTTATTTTAAAAAA
```

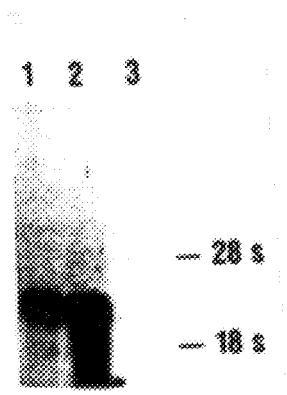

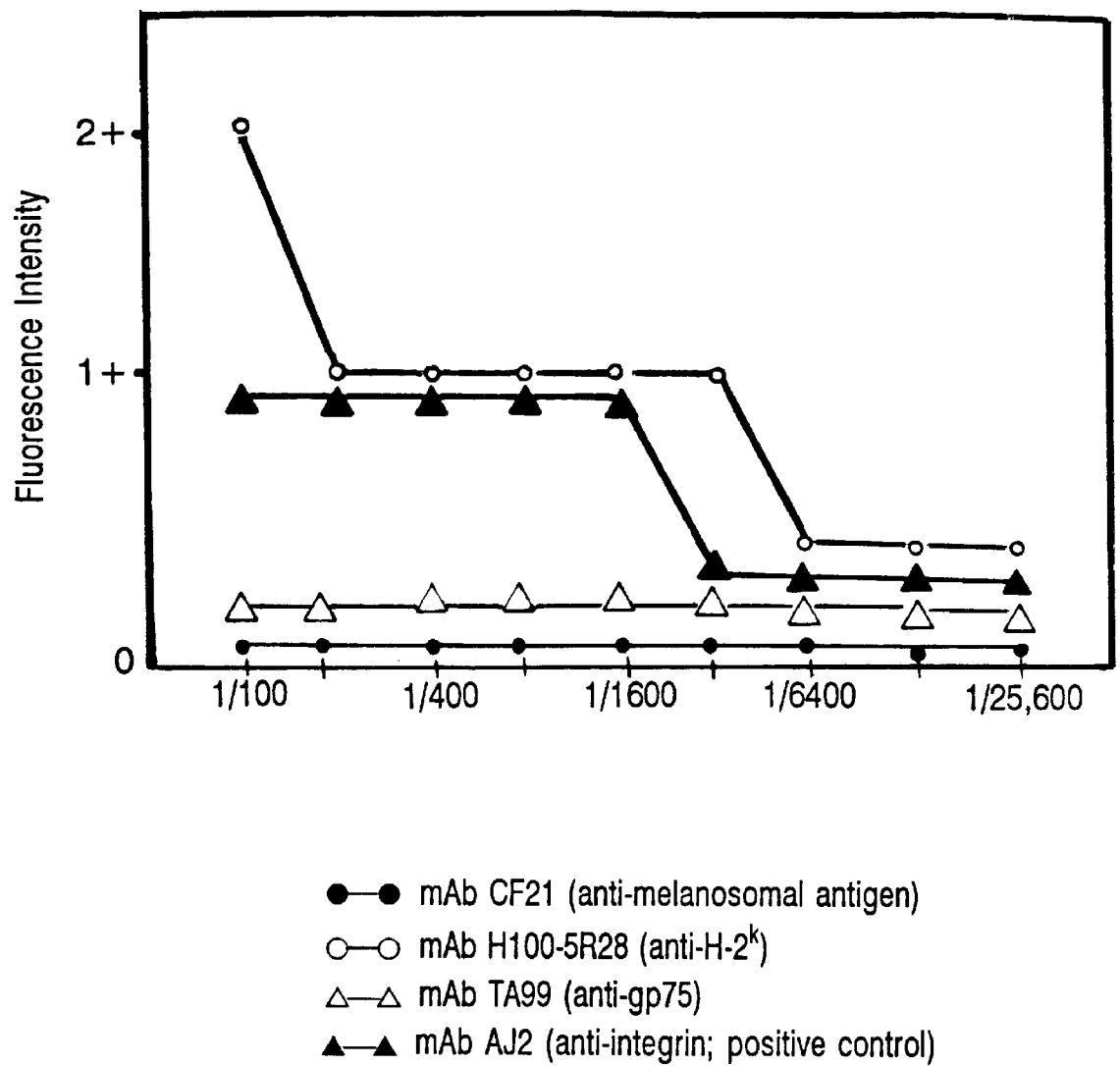

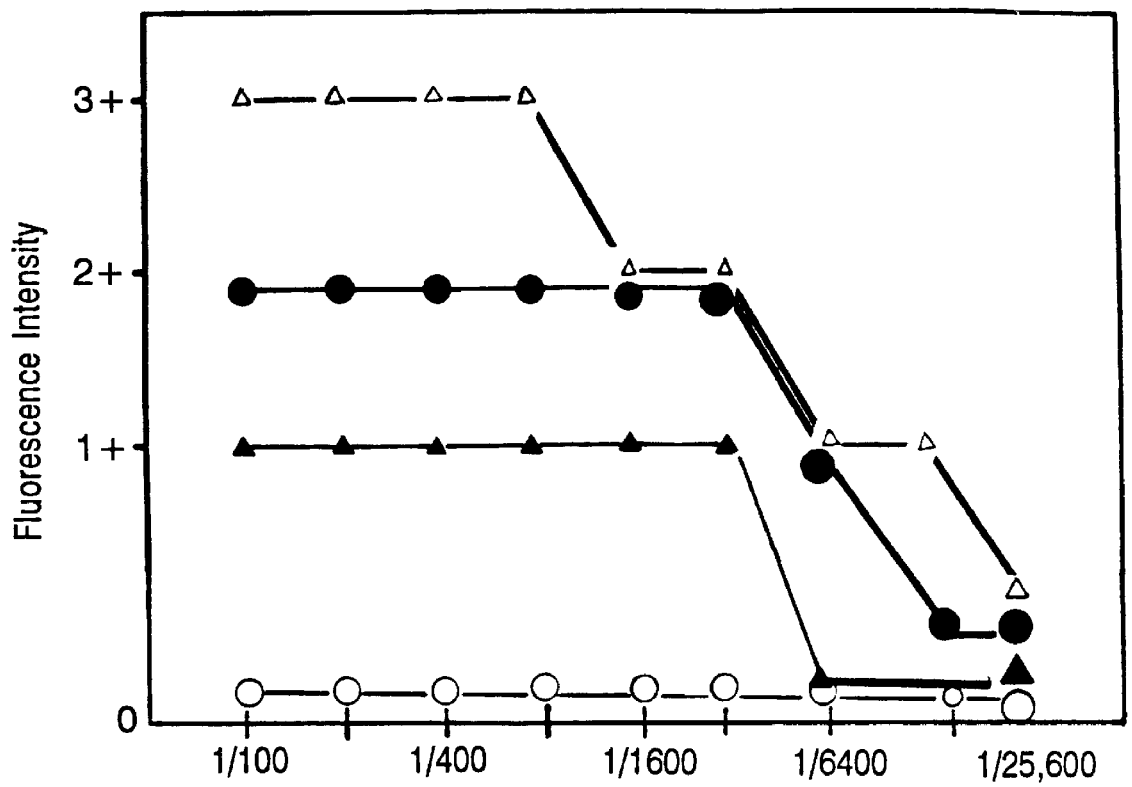

5,773,291

NON-MELANOTYTIC MAMMALIAN CELL CONSTITUTIVELY EXPRESSING BIOLOGICALLY ACTIVE HUMAN TYROSINASE AND USE THEREOF

This is a Continuation of U.S. application Ser. No. 08/166,601, filed Dec. 13, 1993, now abandoned, which is a continuation of U.S. Ser. No. 08/008,255, filed Jan. 25, 1993, now abandoned, which is a continuation of U.S. Ser. No. 07/594,310, filed Oct. 9, 1990, now abandoned, which is a continuation-in-part of U.S. Ser. No. 07/343,960, filed Apr. 26, 1989, now abandoned.

BACKGROUND OF THE INVENTION

Throughout this application, various publications are referenced by Arabic Numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

Melanocytes and cells of melanocyte lineage are distinguished by their capacity to synthesize the pigment melanin. Melanin production is primarily regulated by the enzyme tyrosinase (monophenol, 3, 4-dihydroxyphenylalanine: oxygen oxidoreductase, EC 1.14.18.1).

Melanin synthesis occurs principally in melanosomes which are specialized organelles. Thus, melanin synthesis is generally restricted to melanosome-containing melanocytic cells.

This application describes the isolation of a full length of cDNA clone encoding human tyrosinase. Isolation is achieved by using a probe whose sequence is homologous to the Pmel 34 cDNA sequence described by Kwon et al. (1, 35, 37). Moreover, transfection and expression of this new human tyrosinase cDNA clone in mouse fibroblasts induced pigmentation in a cell type which normally does not synthesize melanin.

Levels of tyrosinase activity in transfected fibroblasts were equivalent to tyrosinase levels in highly pigmented human melanoma cell lines. These tyrosinase-positive fibroblast cell lines demonstrate that melanin synthesis can take place in cells that are not melanosome-containing. As a result, we have a tool in which to study the regulation, transport and processing of tyrosinase synthesis.

SUMMARY OF THE INVENTION

This invention provides a non-melanocytic eucaryotic cell constitutively expressing biologically active human tyrosinase. This invention also provides such a cell which expresses biologically active human tyrosinase under conditions such that the cell produces melanin.

Still further, this invention provides a method of producing biologically active human tyrosinase and melanin.

BRIEF DESCRIPTION OF THE FIGURES

FIGS. 1a–d. Nucleotide and predicated amino acid sequence of BBTY-1 cDNA. The nucleotide sequence is numbered in the 5' to 3' direction. Residues of a predicted signal peptide are indicated by negative numbers, and a cleavage site by a vertical arrow. Termination site (TAA) and polyadenylation signal (869 to 875) are underlined. Potential glycosylation sites are designated by dashed lines.

FIG. 2. Northern blot analysis of poly (A$^+$)-selected RNA (4 $\mu$g/lane) from two pigmented melanoma cell lines that express tyrosinase and the B cell lymphoma cell line Daudi. The blot was hybridized with the $^{32}$P-labeled insert of pBBTY-1. Lanes: 1) SK-MEL-23 melanoma; 2) SK-MEL-19 melanoma; and 3) Daudi.

FIG. 8. Indirect immunofluorescence assays for antigen expression by: A) LpcTYR-2 cells expressing BBTY-1, and B) SK-MEL-19 melanoma cells. mAb TA99 (anti-gp75) △; mAb CF21 (anti-melanosomal antigen) ●; mAb H100-5R28 (anti-H-2$^k$) ○; and mAb AJ2 (anti-integrin; positive control) ▲.

DETAILED DESCRIPTION OF THE INVENTION

Figure 3:
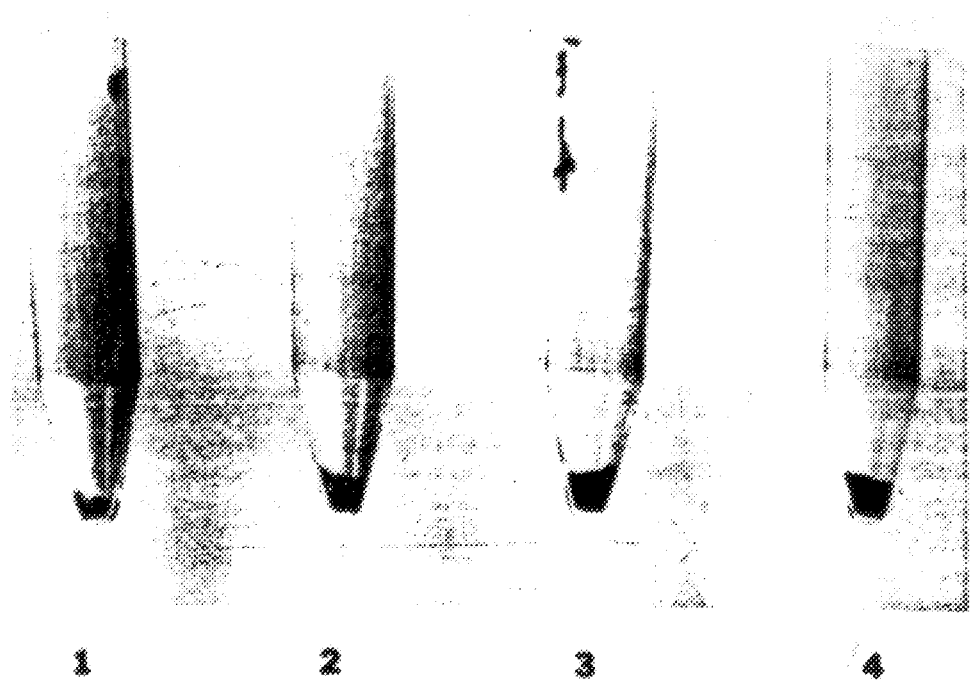
FIG. 3. Cell pellets of L929 cells transfected with sense BBTY-1 (LpcTYR cell line), anti-sense BBTY-1 (LpcTYW cell line), or pUC 18 plasmid (LpC cell line). LpcTYR and LpcTYW cell lines were transfected with BBTY-1 inserted sense or antisense into the expression vector pcEXV3. LpcTYR-1 and LpcTYR-2 are subclones of LpcTYR. 1) LpC cell pellet (non-pigmented); 2) LpcTYW (non-pigmented); 3) LpcTYR-1 (pigmented); and 4) LpcTYR-2 (pigmented).

The present invention provides a non-melanocytic eucaryotic cell constitutively expressing biologically active human tyrosinase.

As used herein "biologically active human tyrosinase" means a polypeptide having (1) an amino acid sequence identical to, or substantially identical to, the amino acid sequence of and (2) the biological activity of naturally occurring human tyrosinase.

Further, as used herein "non-melanocytic eucaryotic cell" means eucaryotic cell characterized by the absence of melanosomes, that is, the organelles associated with the production of the polymeric pigment melanin. On example of such a cell is a fibroblast.

In principle, any eucaryotic cell is useful in the practice of the subject invention including without limitation, mammalian cells such as human cells for example fibroblast cells, the cells of other animals such as ovine, porcine, murine, bovine or avian cells, insect cells, or yeast cells.

Useful non-melanocytic eucaryotic cells include eucaryotic cells in which DNA encoding biologically active human tyrosinase is not naturally present and into which such DNA has been introduced. Methods for introducing such DNA are well known to those skilled in the art as are methods for doing so under conditions such that the DNA will be expressed and biologically active human tyrosinase produced (43).

In one embodiment of the invention, the DNA encoding human tyrosinase is carried on an expression vector suitable for expression in the eucaryotic cell type involved. For example, for a mammalian cell, the expression vector may be a retrovirus; for an insect cell, the expression vector may be a baculovirus. Any nucleic acid encoding biologically active human tyrosinase may be used in this invention. One such DNA is DNA having the sequence shown in FIG. 1 extending from nucleotide 58 to nucleotide 1593 (BBTY-1).

Methods for constructing expression vectors are well known in the art (43). Using such methods DNA encoding a biologically active human tyrosinase is inserted into a suitable expression vector under the control of appropriate regulator sequences. The resulting vectors are then introduced into an appropriate eucaryotic cell, again using methods well known in the art (43) under suitable conditions as to obtain a non-melanocytic eucaryotic cell constitutively expressing biologically active human tyrosinase.

For example, the non-melanocytic eucaryotic cell may be a mammalian cell such as a mouse or human fibroblast cell and may comprise a retroviral expression vector, for example, an expression vector which comprises an SV40 early region promoter and enhancer sequences, an initiation codon immediately upstream of the DNA encoding human tyrosinase, and a termination signal immediately downstream of the DNA encoding human tyrosinase.

Alternatively, the non-melanocytic eucaryotic cell may be an insect cell and may comprise a baculovirus expression vector, for example, an expression vector which comprises DNA encoding biologically active human tyrosinase under the expressional control of a polyhydrin promoter (44).

As yet another alternative, the non-melanocytic eucaryotic cell may be a yeast cell and may comprise an expression plasmid, for example, an expression plasmid which comprises DNA encoding biologically active human tyrosinase under the expressional control of a suitable promoter such as the alcohol dehydrogenase isoenzyme I (ADH I), the phosphoglycerol kinase (PGK) promoter, the repressible acid phosphatase (PHO5) promoter and the a factor promoter (plus the signal sequence).

In a preferred embodiment of this invention the non-melanocytic eucaryotic cells which constitutively produces biologically active human tyrosinase produces melanin.

This invention also provides a method for producing a biologically active human tyrosinase which comprises culturing the cells described hereinabove under conditions such that the cells express the biologically active human tyrosinase and recovering the human tyrosinase so expressed.

Conditions for culturing the cells and for recovering the biologically active human tyrosinase are known in the art and vary depending upon the nature of the eucaryotic cell, expression vector (if any) and the like.

This invention also provides a method for producing a biologically active human tyrosinase which comprises culturing the cells described hereinabove under conditions such that the cells express the biologically active human tyrosinase and recovering the human tyrosinase so expressed.

Additionally, the method of producing melanin which comprises culturing eucaryotic cells under conditions such that the cells express biologically active human tyrosinase and the tyrosinase so expressed catalyzes the production of melanin, and then recovering the melanin so produced.

This invention is illustrated in the Experimental Details section which follows. This section is set forth to aid in an understanding of the invention but is not intended to, and should not be construed to, limit in any way the invention as set forth in the claims which follow.

EXPERIMENTAL DETAILS

MATERIALS AND METHODS

Cell Culture and Cell Lines.

Melanoma cell lines were established as previously described (2). TK'L929 cells (mouse fibroblast) (3) were used for transfection experiments. Cell lines were maintained in Eagle's Minimum Essential Medium supplemented with 2 mM glutamine, 0.1 mM non-essential amino acids, 100 U/ml penicillin, 0.1 mg/ml streptomycin and 10% fetal bovine serum (complete medium). Cells were passaged with trypsin (1 mg/ml and EDTA (0.2 mg/ml). All cultures were checked regularly for the presence of mycoplasma and contaminated cultures were discarded.

Electron Microscopy.

Cell pellets were fixed in Karnofsky's fixative overnight, rinsed in PBS for 1 hour, then post-fixed for 1 hour in 1% osmium tetroxide-PBS solution. Cell pellets were dehydrated in graded ethyl alcohol followed by propylene oxide, and embedded in Maraglas-D.E.R. 732 epoxy resin (Dow Chemical Co., Midland, Mich.). For orientation, 1 $\mu$m thick sections were stained with borate-buffered 1% toluidine blue. Thin sections were stained with uranyl acetate followed by lead citrate and examined with a Philips 410 LS electron microscope.

cDNA Library and Screening.

A cDNA library was constructed from 3 $\mu$g of poly(A+) selected mRNA (4) prepared from the human melanotic melanoma cell line SK-MEL-19 (2). Full length cDNA was synthesized, rendered blunt-ended using Klenow enzyme, and tailed with EcoRI linkers (New England Biolabs, Inc., Beverly, Mass.) (5). The cDNA was then size-fractionated on Ultrogel Aca 34 (Pharmacia Fine Chemicals, Piscataway, N.J.) (6). cDNA molecules>800 bp were used to construct a library of 3×10$^5$ recombinants in the lambda phage vector gt10(7). For screening, a 50 base oligonucleotide probe (50-mer, shown below) based on the 5' terminal coding region of the human tyrosinase Pmel 34 cDNA clone (1) was used.

```
       ..........10........20........30........40........50.
       5'GTTCTTAGAGGGAGACACAGGCTCTAGGGAAAATGGCCAGCGGAGGTCTGGA3'
```

The oligonucleotide was synthesized on an Applied Biosystem DNA synthesizer, model 310 A (Applied Biosystems, Foster City, Calif.). The probe was end-labeled with gamma $^{32}$P-ATP and T4 polynucleotide kinase (4). Prehybridization and hybridization were carried out at 48° C. for 4 hours and 18 hours, respectively, in 6× NET (1× NET is 0.15M NaCl, 1 mM EDTA, and 15mM Tris-HCl, pH 8), 0.1% SDS and 5× Denhardt's solution (0.1% BSA, 0.1% Ficoll 400, 0.1% polyvinylpyrolidone), and 100 µg/ml of denatured salmon sperm DNA. Duplicate filters were washed in 6× NET, 0.1% SDS at room temperature, followed by stringent washes at 55° and 60° C. The filters were then autoradiographed for 4 hours at −70°.

DNA Sequencing.

Plaque purified phage DNA was restricted with EcoRI and cDNA inserts were subcloned into the plasmid vector pUC 18(8). Recombinant plasmids and deletion subclones subsequently obtained by digestion with exonuclease III/Mung Bean nuclease (9) were sequenced by the dideoxynucleotide chain termination method (10).

Northern Blot Analysis.

Poly (A+)-mRNA (4 µg) was fractioned on 1% formaldehyde denaturing agarose gels (4), transferred of Gene Screen Plus membranes (Dupont, New England Nuclear, Boston, Mass.), and hybridized to a $^{32}$P-labeled cDNA probe. The filters were washed twice at room temperature in 2× SSC (1× SSC is 0.15M NaCl, 0.015 M sodium citrate pH 7) and 1% SDS, then stringent washes were carried out at 55° C. in 1× SSC, 1% SDS, and at 65° C. in 0.1× SSC, 1% SDS, for 15 minutes each.

Transfection Experiments.

The cDNA inserts were subcloned into the EcoRI site of the expression vector pcEXV-3, which allows expression of cDNA under the control of SV40 early region promotor and enhancer sequences (11). Expression plasmids containing cDNA inserts in opposite orientations (5'→3' or 3'→5') were constructed. Sense and antisense oriented plasmids were designated pcTYR and pcTYW, respectively. L929 cells were cotransfected by the calcium phosphate precipitation technique (12) with the following combinations: (1) transfection with pUC 18, pSV2 neo plasmid, and high molecular weight carrier DNA from L929 cells; (2) transfection with pcTYR, pSV2 neo plasmid, and high molecular weight carrier DNA from L929 cells; or (3) transfaction with pcTYR, pSV2 neo plasmid, and high molecular weight carrier DNA from L929 cells.

Selection of transfectants was started on day 3 following transfection with 1 mg/ml of the antibiotic G418 (Sigma Chemical Co., St. Louis, Mo.). Complete medium with G418 was replaced every 3 days and colonies appearing on days 10–14 were isolated using cloning rings and expanded. The mouse origin of transfected cell lines was confirmed by positive anti-mouse Ig mixed hemadsorption assays using H-100-5R28, a monoclonal antibody directed against H-2K$^k$ (mouse MHC class I antigens) (13), and lack of reactivity with mAb M3-68 (14) or AJ2 (15) which recognize virtually all human melanoma cells but not L929 cells.

Serological Reagents and Assays.

CF21 (IgG1) and TA99 (IgG2a) are mAb which have been previously described that recognize distinct antigens in human melanosomes (16). The monoclonal antibody 2G10 (IgG2a) recognizes a 75 kD intracellular glycoprotein of pigmented melanotic cells (17). mAb AJ2 (IgG1) recognizes the beta subunit of human VLA/integrin molecules (15, 18). Rabbit anti-tyrosinase antiserum was raised by immunization with purified mouse tyrosinase (19). Tyrosinase was purified by DEAE ion exchange chromatography followed by sequential discontinuous polyacrylamide gel electrophoresis. Anti-mouse immunoglobulin hemadsorption assays and indirect immunofluorescence studies were performed as described (2, 20).

Immunoprecipitations.

Cells were labeled with $^{35}$S-methionine (ICN Radiochemicals, Irvine, Calif.) for 16 hours in methionine-free complete medium containing 2% dialyzed FBS, and lysed in 50mM Tris, 5 mM EDTA, 0.5% NP40, 1 mM PMSF. The lysates were precleared twice by incubation with 5 µg/ml of protein A Sepharose (Pharmacia Fine Chemicals) for 30 minutes at 4° C. Immunoprecipitations were performed by incubating the lysates with antibodies, followed by addition of protein A sepharose. The immunoprecipitates were extensively washed and analyzed for molecular size by SDS/polyacrylamide gel electrophoresis (21) under reducing conditions.

Tyrosinase Activity and Melanin Assays.

Cells were solubilized in PBS, 1% NP40, pH 6.8, and centrifuged to obtain clear supernatants. Tyrosine hydroxylase activity was assayed using a modification of the method described by Pomerantz (22). The reaction mixture contained 1 µCi/ml $^3$H-tyrosine (54.2 Ci/mMol) in PBS, 1% NP40, 0.1 mM L-tyrosine, and 0.1 mM L-DOPA. The reaction was carried out at 37° C. for 1 hour, and terminated by addition of 0.2 ml of a charcoal suspension (100 mg/ml in 0.1 M citric acid). After 30 min on ice, the samples were centrifuged and an aliquot was counted in a Beckman LS 9000 scintillation counter. All assays were performed in duplicate. Controls included $^3$H$_2$O release measured in lysates from the human renal carcinoma cell line SK-RC-7 and reaction mixture in PBS, 1% NP40 alone. Specific tyrosinase activity was calculated as follows: [($^3$H$_2$O release by test cell lysate)—($^3$H$_2$O release by control reaction mixture in PBS)]. Protein concentrations were determined by the Bradford's dye binding method using the Protein Assay Kit (Bio-Rad Laboratories, Richmond, Calif.). For melanin assays, 3×10$^6$ cells were solubilized in 0.5 ml Protosol (NEN, DuPont, Boston, Mass.) and kept on ice for 2 hours. An absorption baseline was established using Protosol, and absorption spectra for cell extracts were determined between 320–450 nm and compared against a melanin control 100 µg/ml, in Protosol.

RESULTS

Isolation and Sequencing of the CDNA Clone BBTY-1.

CDNA clones were isolated from a lambda gt10 library derived from the pigmented human melanoma cell line SK-MEL-19 (see Materials and Methods). 10$^5$ recombinant CDNA clones were screened and four reactive clones were plaque purified. The four cDNA inserts were subcloned into the plasmid vector pUC 18 and clones were designated pBBTY-1, -2, -3, and -4. Two clones, pBBTY-1 and pBBTY-2, each containing cDNA inserts of 2 kb, had restriction maps identical to each other and to that of Pmel 34 reported by Kwon et al. (1) (digested with Bgl II, Hpa II, Msp I, Nco I, Pvu II, and Taq I). The cDNA inserts in clones pBBTY-3 and pBBTY-4 were 1.7 and 1.8 kb, respectively. The restriction map of pBBTY-3 was different from those of pBBTY-1 and pBBTY-2 downstream of position 960 (a PvuII restriction site). pBBTY-1 was subsequently sequenced and used for further experiments.

The nucleotide sequence of BBTY-1 (FIG. 1) contained a single open reading frame of 1593 residues capable of encoding a 531 amino acid (aa) polypeptide with a derived molecular weight of 60.37 kD. A leader peptide of 19 aa was assigned to positions -19 through -1 (23). The processed core protein was predicted to have a molecular weight of 58.118 kD. Seven potential N-glycosylation signals (Asn-X-Ser/Thr) were predicted at positions 69, 94, 144, 213, 273, 320, and 354. Based on a hydrophobicity plot according to the method of Kyte-Doolittle (24), a transmembrane region was predicted within a highly hydrophobic domain between aa positions 460 and 480. There was a 318 base 3' non-coding region that contained an atypical polyadenylation signal AATTAAA (25). The nucleotide and aa sequence of BBTY-1 were nearly identical to the sequence of the Pmel 34 CDNA (1). However, BBTY-1 contained an additional upstream 5' sequence, including a potential initiation codon not present in Pmel 34 (bases 1 to 7). There were also differences in the predicted amino acid sequence of BBTY-1 at positions 25–28, 162, 291, 356–361, 385, 478 and 503–512. The predicted molecular size of the processed protein coded by BBTY-1 was smaller than the processed protein predicted from Pmel 34 (62.16 kD). Based on this sequence analysis, BBTY-1 was a candidate for a full length CDNA clone encompassing a complete coding region.

Transcription of BBTY-1 in Human Melanoma Cells.

BBTY-1 cDNA was used to detect mRNA transcripts in Northern blot analysis of a panel of melanoma cell lines, including those known to express tyrosinase activity as well as tyrosinase-negative melanomas. The major transcript detected was 2.4 kb, but a weaker signal was seen at 4.7 kb (FIG. 2). Three groups of melanomas were observed based on Northern blot analysis using poly $(A^+)$-selected RNA: (a) mRNA was detected in 9 pigmented melanomas that express tyrosinase activity; (b) no mRNA was detected in 5 non-pigmented, tyrosinase-negative melanomas; (c) mRNA was detected in 3 non-pigmented tyrosinase-negative melanomas. There was little or no difference in the intensity of mRNA signal detected group; (c) versus (a). No transcript was detected in mRNA from the B cell lymphoma cell line Daudi or from the T cell leukemia cell line HUT-78.

Melanin Synthesis in L929 Cells Transfected With BBTY-1.

BBTY-1 was transfected into L929 mouse fibroblasts using the expression vector pcEXV-3 (11). L929 cells transfected with pcTYR (sense orientation) were designated LpcTYR. Control cells transfected with pcTYW (antisense orientation) were designated LpcTYW, and with the plasmid pUC 18 were designated LpC. LpcTYR cells contained pigment, while no pigmentation was detected in LpcTYW, LpC or untransfected L929 cells. As shown in FIG. 3, the cell pellets of LpcTYR clones were dark brown in contrast to the non-pigmented pellets of LpcTYW and LpC cultures.

Cell pellets of LpcTYR were more deeply pigmented when cultures were harvested at confluency. LpcTYR clones have continued to produce pigment for more than 5 months in continuous culture. In order to confirm that the pigment in LpcTYR has the characteristics of melanin, absorption spectra of cell extracts from LpcTYR and control L929 cells were compared to those of extracts of the pigmented melanoma cell line SK-MEL-19 and purified melanin. LpcTYR and SK-MEL-19 extracts and melanin had identical patterns of absorption, with broad absorption from 360 nm to >450 nm; this absorption pattern was not observed with L929 cell extracts. The absorption patterns by extracts of LpcTYR and SK-MEL-19 and melanin standard were identical to the previously described absorption spectra for melanin (26).

Figure 4:
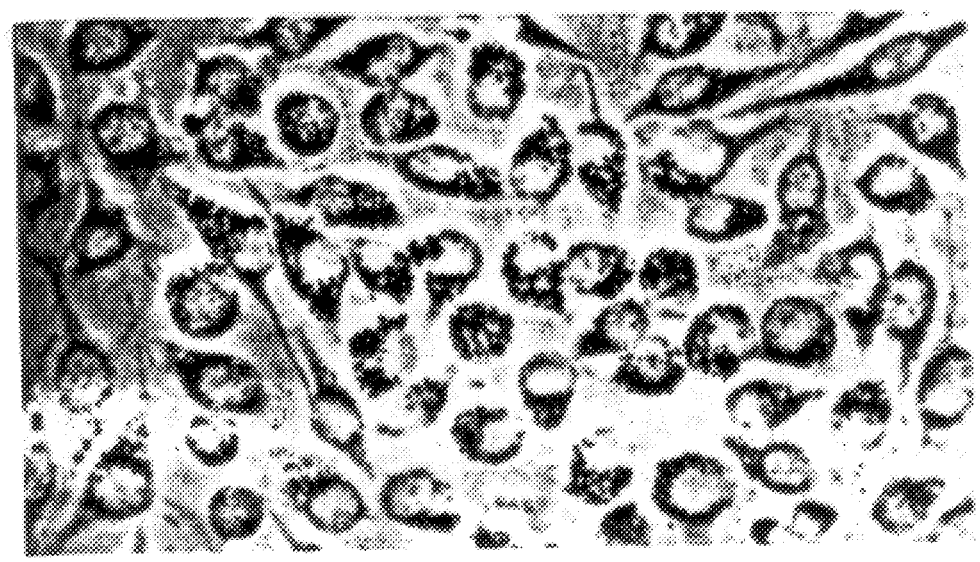
FIG. 4. LpcTYR cells in culture. A nest of cells in the middle of the field contains large, pigmented cytoplasmic granules. Magnification ×320.

Small clusters of cells containing dark cytoplasmic inclusions were observed throughout the LpcTYR culture by light microscopy (FIG. 4)—these clusters of cells always comprised a minority of the culture population.

Occasional black, round cells were detected floating in the tissue culture medium, perhaps related to cytostatic or cytotoxic effects of melanin by-products, and the prevalence of these cells increased as the culture reached confluency.

Figure 5A:
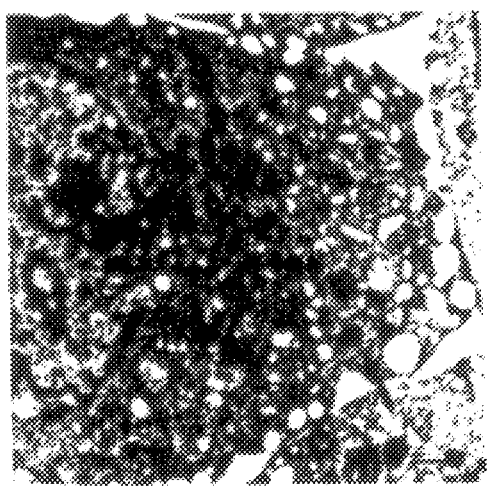
FIG. 5. Transmission election micrographs of segments of LpcTYR cells. A) Cytoplasmic membrane-bound vesicles containing electron dense material are indicated by arrows. One scale bar represents 1 $\mu$m. Magnification ×8,400. B) Higher magnification field of a cytoplasmic membrane-bound vesicle containing pigment. One scale bar represents 1 $\mu$m. Magnification ×16,800.
Figure 5B:
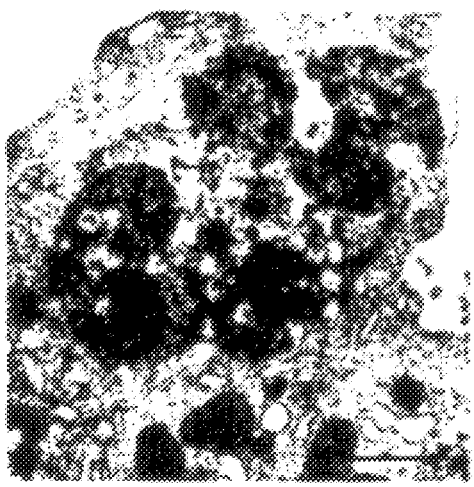

Transmission electron microscopy revealed that LpcTYR cells, but not control LpC cells, had cytoplasmic membrane-bound vesicles (FIG. 5) containing electron dense material consistent with melanin. There was no evidence of melanosomal structural elements within LpcTYR cells or Lpc cells.

Tyrosinase Activity In L929 Cells Expressing BBTY-1.

Figure 6:
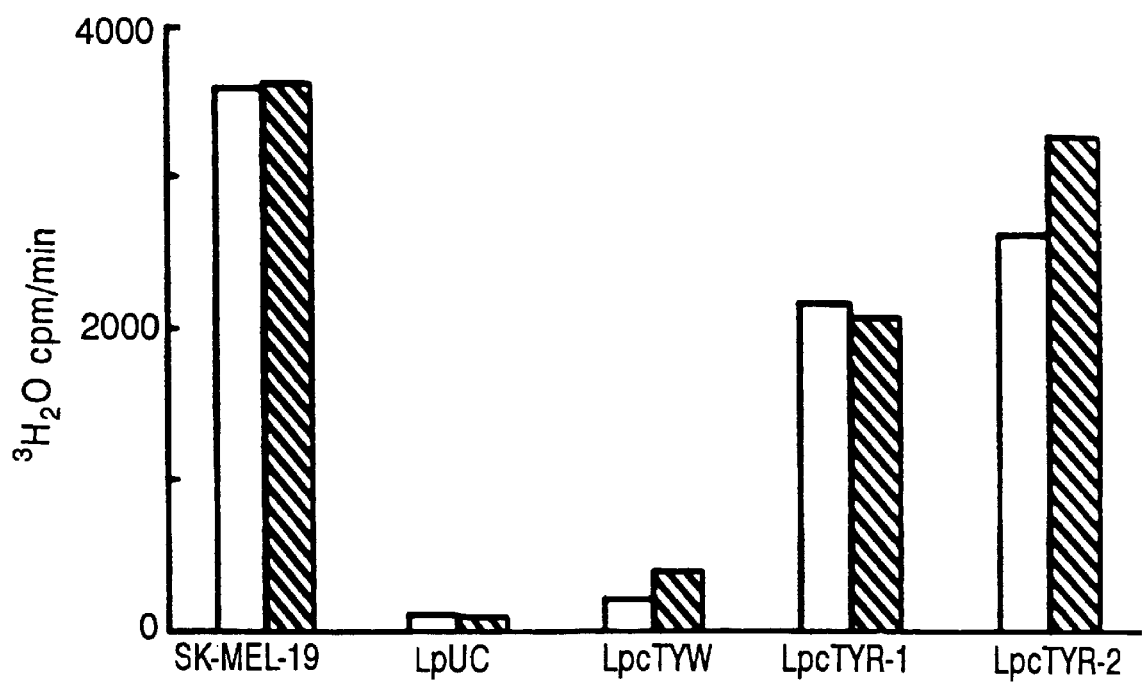
FIG. 6. Expression of tyrosinase activity in cell extracts from: 1) SK-MEL 19 melanoma; 2) Lpc cells (transfected with pUC 18 plasmid); 3) LpcTYR-l cells (transfected with BBTY-1 sense construct) 4) LpcTYR-2 cells (transfected with BBTY-1 sense construct); and 5) LpcTYW cells (transfected with a BBTY 1 antisense construct). Tyrosine hydroxylase activity is expressed as (cpm $^3$H$_2$O/min/mg protein) [▭ bars] or (cpm $^3$H$_2$O/min/5×10$^6$ cells) [▨ bars].

To confirm that the BBTY-1 product was human tyrosinase, tyrosine hydroxylase activity was measured in protein extracts of subclones of LpcTYR, LpcTYW and LpC. Cell extracts from two subclones of LpcTYR, designated LpcTYR-1 and LpcTYR-2, expressed levels of tyrosinase activity that were comparable to levels in the pigmented human melanoma cell line SK-MEL-19 (FIG. 6). In contrast, extracts of LpcTYW and LpC contained no detectable tyrosinase activity.

Analysis of Expression of Melanosomal Antigens in Lpc-TYR Cells.

Figure 7:
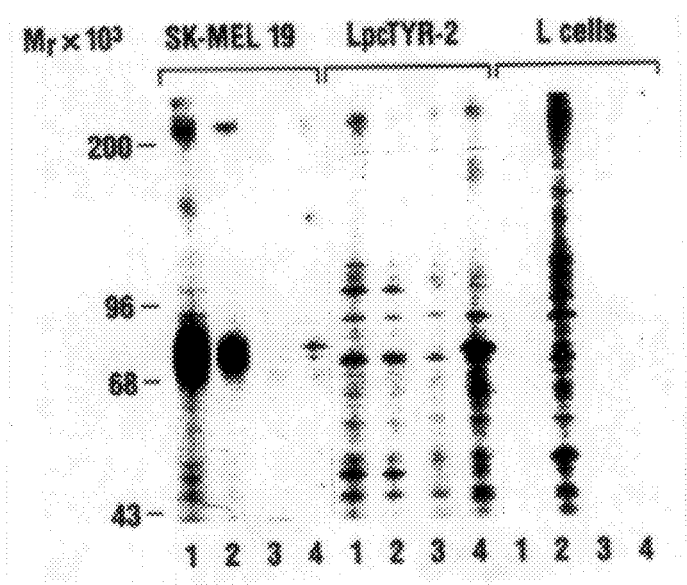
FIG. 7. Immunoprecipitation of lysates from $^{35}$S-methionine metabolically labeled SK-MEL-19 melanoma cells, LpcTYR-2 cells expressing BBTY-1, and L929 cells. Lanes: 1) mAb TA99; 2) mAb 2G10; 3) control rabbit sera; and 4) rabbit anti-tyrosinase antisera. A 75 kD band is detected in SK-MEL-19 (with TA99, 2G10 and anti-tyrosinase) and LpcTYR-2 cells (with anti-tyrosinase). Molecular weight standards: Myosin M chain (200 kD); phosphorylase (96 kD); bovine serum albumin (68 kD); and ovalbumin (43 kD).

LpcTYR-2, SK-MEL-19 melanoma cells and control L929 cells were metabolically labeled with $^{35}$S-methionine and cell extracts were immunoprecipitated with rabbit anti-tyrosinase antiserum or mAb TA99 (which detects the melanosomal antigen gp75). In addition, mAb 2G10 which is also directed against an intracellular 75 kD antigen expressed by pigmented melanoma cells (17) was tested. Anti-tyrosinase antiserum detected a 75 kD protein in LpcTYR-2 cells and a protein of the same size in SK-MEL-19 melanoma cells (FIG. 7). The molecular size of tyrosinase in LpcTYR-2 and SK-MEL-19 cells corresponded to the size of glycosylated tyrosinase. A very faint band at approximately 75 kD was inconsistently detected in L929 cells with anti-tyrosinase antiserum—this likely represents a cross-reaction of polyclonal sera to a non-tyrosinase molecule in L929 cells since no tyrosinase activity or tyrosinase transcript was detected in these cells and cold lysates from L929 cells did not block immunoprecipitation of tyrosinase from LpcTYR-2.

No specific bands were detected by either mAb TA99 or mAb 2G10 in LpcTYR-2 extracts, although both antibodies precipitated a broad 75 kD band from melanoma SK-MEL-19 lysates. These results were confirmed using immunofluorescence assays. Neither mAb TA99 nor 2G10 stained LpcTYR cells but both reacted with SK-MEL-19 cells (FIG. 8). In addition, mAb CF21, directed against a melanosomal antigen of unknown molecular size, did not react with LpcTYR but stained SK-MEL-19 (FIG. 8). Accordingly, mAb TA99, CF21 and 2G10 appear to identify antigens distinct from tyrosinase encoded by BBTY-1 cDNA clone.

DISCUSSION

Tyrosinase catalyzes the 2-hydroylation of monophenols and oxidation of 2-diphenols to 2-quinones. In melanocytic cells, tyrosinase enzymatically converts tyrosine to dihydroxyphenylalanine (DOPA) and DOPA to dopaquinone, leading to the spontaneous formation of the complex mixture of pigments known as melanin (27). The later steps in this pathway are not well characterized, and it has been suggested that a number of other factors, both catalytic and inhibitory, may regulate melanin synthesis and influence the species of melanin formed (28, 29). The complexity of pigment expression has been further highlighted by genetic studies in the mouse where more than 50 loci have been found to influence coat color (30). Thus, it is possible that a number of gene products, most not yet identified, can play a role in melanogenesis.

It is remarkable that transfected L929 fibroblasts not only stably expressed tyrosinase activity but were able to produce and package melanin. Melanin precursors are cytotoxic, and it has been presumed that melanocytic cells contain mechanisms, perhaps located within melanosomes, that protect from the effects of toxic intermediates. Melanin precursors were cytotoxic in transfected L929 cells, and that cells producing substantial amounts of pigment were destined to die, based on the following observations: (1) only a subpopulation of transfected cells contained pigmented vesicles; (2) deeply pigmented, non-viable cells were observed floating in the supernatant of transfectant cultures; and (3) when transfected cells were cryopreserved and then thawed, pigmented cells were not initially detected but eventually repopulated the culture.

The details involving the synthesis or processing of human tyrosinase in transfected L929 cells has not been analyzed. It appears that human tyrosinase is glycosylated to a form identical in size to fully processed tyrosinase expressed in human melanocytic cells. It is likely that human tyrosinase was processed through the Golgi apparatus in L929 cells and transported to or remaining in vesicles arising from the trans Golgi. The nature and destination of these vesicles is not known. It is interesting to speculate that these vesicles might be precursors of melanosomes but that formation of melanosomes would depend on the products of other specialized genes.

The expression and regulation of tyrosinase has been the subject of extensive studies, but the formal identification of the gene that codes for tyrosinase has not been straightforward (reviewed in 31). Two distinct, and distantly related, genes have been proposed as candidates for mouse tyrosinase, based on detection of mRNA of these genes in melanocytic cells and reactivity of the protein product with antibodies against tyrosinase (32, 33). Neither gene, however, was demonstrated to directly code for a product with tyrosinase activity. It is likely that antibodies used to detect the products of putative tyrosinase cDNA clones reacted with other molecules that copurified with tyrosinase. This situation was recently clarified by the identification of the mouse tyrosinase gene by Muller et al. who isolated a cDNA clone, pmctyrl, that coded for transient expression of tyrosinase activity in transfection assays (34). No pigment synthesis was reported in transfected cells, possibly because assays were performed only shortly after transfection, because the recipient cells were different (an amelanotic melanoma and a breast carcinoma cell line), or because levels of tyrosinase activity appeared to be much lower than in mouse fibroblasts transfected with BBTY-1.

The candidates for the human tyrosinase gene, designated Pmel 34, has been reported by Kwon et al. (1). Kwon and coworkers also recently described a mouse cDNA, MTY811C, isolated using Pmel 34 (35). The gene product encoded by MTY811C was predicted to be 81% homologous to the protein encoded by Pmel 34. Both the human Pmel 34 and the mouse MTY811C correspond to the human counterpart of the mouse pmctyrl gene, and in fact the pmctyrl clone was also isolated by screening a CDNA library from mouse melanoma cells with the Pmel 34 cDNA. The Pmel 34 cDNA clone was detected by screening a cDNA library with polyclonal antisera raised against hamster tyrosinase. Pmel 34 has been mapped to the c-albino locus in the mouse, the presumed site of the tyrosinase structural gene or a gene that regulates tyrosinase expression. The nucleotide and predicted aa sequences of BBTY-1 and Pmel 34 are closely similar, except BBTY-1 contains an initiation codon that is not present in Pmel 34. Additionally, there are minor differences in nucleotide and predicted aa sequences. It is possible that some of these differences represent genetic polymorphism or somatic mutations (related to the source of cell types used to isolate cDNA—melanoma cells for BBTY-1 versus melanocytes for Pmel 34). It is interesting to note that, where there are distinct differences in sequences between BBTY-1 and Pmel 34, the sequence of BBTY-1 is very close or identical to the mouse pmctyrl tyrosinase sequence (e.g., amino acids, 356–361, and 385).

Multiple transcripts of the tyrosinase gene have been found in mouse melanoma cells (36). The remaining transcripts are generated by alternative splicing leading to deletion of internal sequences, presumably by exon skipping or by selection of internal splice sites. When these alternative transcripts have been expressed, they have not been found to encode active tyrosinase (34, 36). The BBTY-1 cDNA represents the human counterpart of the mouse pmc-Tyrl transcript. Another cDNA clone which was isolated, BBTY-3, differs from BBTY-1 in its 3' restriction map, possibly corresponding to an alternative transcript of the human tyrosinase gene.

As to the relationship of tyrosinase to the melanosomal/cytoplasmic antigens recognized by mAb 2G10, TA99, and CF21, researchers have shown that mAb 2G10 immunodepletes tyrosinase activity (37) and therefore possibly recognizes a molecule with tyrosinase activity. However, mAb 2G10 did not react with human tyrosinase encoded by BBTY-1, suggesting that mAb 2G10 recognizes a distinct molecule from the gene product of BBTY-1. TA99 mAb recognizes an acidic 75 kD glycoprotein (38), and the antigen recognized by TA99 is a candidate for tyrosinase, based on its expression in melanosomes, its molecular size and charge. The finding that mAb TA99 and CF21 did not react with L929 transfectants provides evidence that they do not recognize determinants coded for by the BBTY-1 human tyrosinase molecule. Further data suggest that mAb TA99 does not recognize tyrosinase: 1) mAb TA99 does not precipitate tyrosinase activity from melanoma cell extracts (39, 40); 2) the TA99 antigen, gp75, is generally coexpressed with tyrosinase activity, but there are examples of gp75$^+$ melanoma cell lines that do note express tyrosinase activity; and 3) the expression of tyrosinase and gp75 in melanoma cell lines has been independently regulated (20). Understanding the specificity of monoclonal antibodies that react with melanosomal antigens will be important for sorting out the identity of these molecules. It has been proposed in a recent report by Jimenez et al. that a second gene only distantly related to BBTY-1 and Pmel 34 (33), mapping to the b (brown) locus in the mouse (41), codes for a gene product with tyrosinase activity (42). Thus, it is becoming increasingly evident that tyrosinase is a member of a family of related molecules that include distinct genes and alternative transcripts of these genes (32–34, 36, 41, 42).

SUMMARY

A distinguishing characteristic of cells of the melanocyte lineage is the expression of the melanosomal enzyme tyrosinase which catalyzes the synthesis of the pigment melanin. A tyrosinase cDNA clone, designated BBTY-1, was isolated from a library constructed from the pigmented TA99$^+$/CF21$^+$ melanoma cell line SK-MEL-19, expression of BBTY-1 in mouse L929 fibroblasts led to synthesis and expression of active tyrosinase, and, unexpectedly, to stable production of melanin. Melanin was synthesized and stored within membrane-bound vesicles in the cytoplasm of transfected fibroblasts. BBTY-1 detected a 2.4 kb mRNA transcript in 9 of 9 pigmented, tyrosinase-positive melanoma cell lines. Tyrosinase transcripts of the same size were detected in a subset (3 of 8) of non-pigmented, tyrosinase-negative melanoma cell lines, suggesting that post-transcriptional events are important in regulating tyrosinase activity. Two melanocyte antigens, recognized by monoclonal antibodies TA99 and CF21, that are specifically located within melanosomes and are co-expressed with tyrosinase activity did not react with transfected mouse fibroblasts expressing human tyrosinase, supporting the conclusion that these antigenic determinants are distinct from the tyrosinase molecule coded for by BBTY-1.

REFERENCE

1. Kwon, B. S., et al., (1987) Isolation and sequence of CDNA clone for human tyrosinase that maps at the mouse c-albino locus, Proc. Natl. Acad. Sci. USA 84: 7473.
2. Houghton, A. N., et al. (1982) Surface antigens of melanocytes and melanoma: markers of melanocyte differentiation and melanoma subsets, J. Exp. Med. 156: 1755.
3. Kit, S., et al. (1963) Deletion of thymidine kinase activity from L cells resistant to bromodeoxyuridine. Exp. Cell. Res. 21: 297.
4. Maniatis, T., et al., *Molecular Cloning, A Laboratory Manual*. Cold Spring Harbor Laboratory Press, Cold Spring Harbor, New York (1982).
5. Gubler, U., Hoffman, B. J. (1963) A simple and very efficient method of generating cDNA libraries, Gene 25: 263.
6. Watson, C. J., and Jackson, J. F. (1985) Constructing and Screening cDNA Libraries in k gt 11 in DNA Cloning: A Practical Approach, D. M. Glover (ed), IRL Press, Oxford 1: 79.
7. Huynh, T. V., et al., An Alternative Procedure for the Synthesis of Double Stranded cDNA for Cloning in Phage and Plasmid Vectors in DNA Cloning: A Practical Approach, D. M. Glover (ed), IRL Press, Oxford 1: 49 (1985).
8. Vieira, J. and Messing, J. (1982) The pUC plasmids and M13Mp7-derived system for insertion mutagenesis and sequencing with synthetic universal primers, Gene 19: 259.
9. Henifoff, S. (1984) Unidirectional digestion with Exonuclease III creates targeted breakpoints for DNA sequencing, Gene 28: 351.
10. Sanger, F., et al. (1977) DNA sequencing with chain termination inhibitors, Proc. Natl. Acad. Sci. USA 74: 5463.
11. Miller, J. and Germain, R. N. (1986) Efficient cell surface expression of class II MHC molecules in the absence of associated invariant chain, J. Exp. Med. 16: 1478.
12. Wigler, M., et al., (1979) Transformation of mammalian cells with genes from procaryotes and eucaryotes, Cell 16: 777.
13. Lemke, H., et al., (1979) Fine specificity analysis with monoclonal antibodies of antigens controlled by the MHC Qa/T1 region in mice, Immunol. Rev. 47: 175.
14. Real, F. X., et al., (1985) Surface antigens of melanomas and melanocytes defined by mouse monoclonal antibodies: specificity analysis and comparison of antigen expression in cultured cells an tissues, Cancer Res. 45: 4401.
15. Cairncross, J. G., et al., (1982) Cell Surface antigens of human astrocytoma defined by mouse monoclonal antibodies: identification of astrocytoma subsets, Proc. Natl. Acad. Sci. USA 79: 5641.
16. Thomson, T. M., et al., (1988) Differentiation antigens of melanocytes and melanoma: analysis of melanosome and cell surface markers of human pigmented cells with monoclonal antibodies, J. Inv. Dermatol. 90: 459.
17. Natali, P. G., et al., (1986) A melanocyte differentiation antigen recognized by a new murine monoclonal antibody mAB, J. Invest. Dermatol. 87: 392.
18. Kantor, R. R. S., et al., (1987) Biochemical analysis of two cell surface glycoprotein complexes, very common antigen 1 and very common antigen 2, J. Biol. Chem. 262: 31.
19. Fuller, B. B., et al., (1987) Melanocyte-stimulating hormone regulation of tyrosine in Cloudman S-91 mouse melanoma cell cultures, J. Biol. Chem. 262: 4024.
20. Houghton, A. N., et al., (1987) Phenotypic heterogeneity of melanoma: relation to the differentiation program of melanoma cells, J. Exp. Med. 164: 812.
21. Laemmli, U. K., (1970) Cleavage of structural proteins during assembly of the head of bacteriophage T4, Nature 227: 680.
22. Pomerantz, S. H., (1969) L-Tyrosine-3, $5'$-$^3$H assay for tyrosinase development in skin of new born hamsters, Science 164: 838.
23. Von Heigne, G., (1983) Patterns of amino acids near signal sequencing cleavage sites, Eur. J. Biochem. 133: 17.
24. Kyter, J. and Doolittle, R., (1982) A simple method for displaying the hydropathic character of a protein, J. Mol. Biol. 157: 105.
25. Wilkins, M. and Stephenson, P., (1984) Role of the conserved AAU-AAA sequence from AAUAAA point mutants prevent mRNA 3' end formation, Science 226: 1045.
26. Oikawa, A. and Nakayasu, M., (1973) Quantitative measurement of melanin as tyrosine equivalents and as weight of purified melanin, Yale J. Biol. Med. 46: 500.
27. Mason, H. S., (1948) The chemistry of melanin III. Mechanism of the oxidation of dihydroxyphenylalanine and tyrosinase, J. Biol. Chem. 172: 83.
28. Pawelek, J. and Lerner, A. B., (1978) 5-6 dihydroxyindole is a melanin precursor showing potent cytotoxicity, Nature 27: 627.
29. Pawelek, J., (1980) New regulators of melanin biosynthesis and the autodestruction of melanoma cells, Nature 186: 617.
30. Silvers, W. K., (1979) The Coat Colors of Mice: A Model for Mammalian Gene Action and Interaction, Springer, Berlin.
31. Hearing, V. J. and Jimenez, M., (1989) Analysis of mammalian pigmentation at the molecular level, Pigment Cell Res. 2: 75–85.
32. Yamamoto, H., et al., (1987) Cloning and sequencing of mouse tyrosinase CDNA, Jpn. J. Genet. 62: 271.
33. Shibahara, S., et al., (1986) Cloning and expression of CDNA encoding mouse tyrosinase, Nucl. Acid. Res. 14: 2413.
34. Muller, G. S., et al., (1988) Functional analysis of alternatively spliced tyrosinase gene transcripts, EMBO J. 7: 2723.
35. Kwon, B. S., et al., (1988) Sequence analysis of mouse tyrosinase cDNA and the effect of melanotropin on its gene expression, Biochem. Biophys. Res. Commun. 153: 1301.

36. Ruppert, S., et al., (1988) Multiple transcripts of the mouse tyrosinase gene are generated by alternative splicing, EMBO J. 7: 2715.
37. Kwon, B.S., et al., (1987) A melanocyte-specific complementary cDNA clone whose expression is inducible by melanotropin and isobutylmethyl zanthine, Mol. Biol. Med. 4: 339.
38. Tai, T., et al., (1983) Glycoproteins as differentiation markers in human malignant melanoma and melanocytes, Cancer Res. 43: 2773.
39. Mattes, J., et al., (1983) A pigmentation-associated, differentiation antigen of human melanoma defined by precipitating antibody in human serum, Int. J. Cancer 32: 717.
40. Thomson, T. M., et al., (1985) Pigmentation-associated glycoprotein of human melanomas and melanocytes: definition with a mouse monoclonal antibody, J. Inv. Derm. 85: 169.
41. Jackson, I. T., (1988) A cDNA encoding tyrosinase-related protein maps to the brown locus in mouse, Proc. Natl. Acad. Sci. USA 85: 4392.
42. Jimenez, M., et al., (1989) Specific identification of an authentic clone for mammalian tyrosinase, J. Biol. Chem. 264: 3397–3403.
43. Winnacker, E-L., (1988) From Genes to Clones, Introduction to Gene Technology.
44. Smith, et al., U.S. Pat. No. 4,745,051, issued May 17, 1988.

What is claimed is:

1. A non-melanocytic mammalian cell constitutively expressing a biologically active human tyrosinase which produces and packages melanin.

2. A method of producing biologically active human tyrosinase which comprises culturing cells of claim 1 under conditions such that the cells express biologically active human tyrosinase and recovering the human tyrosinase so expressed.

3. A method of producing melanin which comprises culturing cells of claim 1 under conditions such that the cells express biologically active human tyrosinase and the tyrosinase so expressed catalyzes the production of melanin and then recovering the melanin so produced.

4. The non-melanocytic mammalian cell of claim 1 comprising an expression vector for said human tyrosinase.

5. The non-melanocytic mammalian cell of claim 4, wherein the vector comprises DNA having the sequence shown in FIG. 1 beginning with guanine at position 58 and ending with adenosine at position 1593.

6. The non-melanocytic mammalian cell of claim 4, wherein the vector further comprises SV40 early region promoter and enhancer sequences, an initiation codon immediately upstream of the DNA encoding human tyrosinase, and a termination signal immediately downstream of the DNA encoding human tyrosinase.

7. The non-melanocytic mammalian cell of claim 4, wherein the vector further comprises a baculovirus.

* * * * *